US006809226B1

United States Patent
Pennetreau et al.

(10) Patent No.: US 6,809,226 B1
(45) Date of Patent: Oct. 26, 2004

(54) PROCESS FOR THE PREPARATION OF 1-CHLORO-1-FLUOROETHANE AND/OR 1,1-DIFLUOROETHANE

(75) Inventors: Pascal Pennetreau, Rixensart (BE); Francine Janssens, Vilvoorde (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 08/549,322

(22) Filed: Oct. 27, 1995

Related U.S. Application Data

(63) Continuation of application No. 08/285,015, filed on Aug. 2, 1994, now abandoned.

(30) Foreign Application Priority Data

Aug. 4, 1993 (BE) .............................................. 9300816

(51) Int. Cl.[7] .............................................. C07C 17/00
(52) U.S. Cl. ...................................... 570/164; 570/123
(58) Field of Search ................................ 570/168, 169, 570/170

(56) References Cited

U.S. PATENT DOCUMENTS 2,495,407 A    1/1950    Chapman et al.

5,008,474 A    4/1991    Wairaevens et al.

FOREIGN PATENT DOCUMENTS

| CN | 1069019 | 2/1993 | |
| DE | 859887 | 12/1952 | |
| FR | 1396251 | 3/1965 | |
| FR | 2019507 | 7/1970 | |
| FR | 2365542 | 4/1978 | |
| GB | 921254 | 3/1963 | |
| GB | 1036354 | 7/1966 | |
| WO | 8912617 | * 12/1989 | ................. 570/168 |

OTHER PUBLICATIONS

Lovelace Aliphodic Fluorine Compounds (1958) pp 12–14.*

* cited by examiner

Primary Examiner—Johann Richter
Assistant Examiner—Karl Puttlitz
(74) Attorney, Agent, or Firm—Connolly Bove Lodge & Hutz LLP

(57) ABSTRACT

The invention relates to a process for the preparation of chloro-1-fluoroethane and 1,1-difluoroethane by reaction of vinyl chloride with hydrogen fluoride, in organic solvent consisting of at least one saturated halogen-containing hydrocarbon.

29 Claims, No Drawings

PROCESS FOR THE PREPARATION OF 1-CHLORO-1-FLUOROETHANE AND/OR 1,1-DIFLUOROETHANE

This application is a Continuation of application Ser. No. 08/285,015, Filed Aug. 2, 1994 now abandon.

FIELD OF THE INVENTION

The present invention relates to a process for the preparation of 1-chloro-1-fluoroethane (HFA-151a) and/or 1,1-difluoroethane (HFA-152a), starting from vinyl chloride, performed in the liquid phase in an organic solvent.

TECHNOLOGY REVIEW

It is known to prepare 1-chloro-1-fluoroethane by reaction between vinyl chloride and hydrogen fluoride in the liquid phase.

For example, in Patent DE 859,887, 1-chloro-1-fluoroethane is obtained by reaction between vinyl chloride and hydrogen fluoride, in the absence of catalyst, simply by introducing the reactants into an autoclave, in which they are heated moderately under autogenous pressure. This process leads, however, to the formation of a larger amount of oily side products.

U.S. Pat. No. 2,495,407 teaches the preparation of 1-chloro-1-fluoroethane starting from vinyl chloride in the presence of tin halide. In the various examples, the reactants are loaded into an autoclave with the desired amount of catalyst and are then subjected to a temperature close to 40° C., under autogenous pressure. This patent also reports some unsuccessful attempts which were performed in the presence of acetic acid or acetone as solvent.

It has nevertheless been observed that these known processes lead to the formation, sometimes in very large amounts, of heavy halogen-containing side products which are mainly formed of oligomers of vinyl chloride, which partly contain fluorine. The formation of these side products seriously affects the reaction yields of 1-chloro-1-fluoroethane and of 1,1-difluoroethane. In addition, the clean destruction of these halogen-containing side products requires the implementation of difficult and very expensive techniques.

Patent FR 1,396,251 has proposed a process for the manufacture of halogen-containing derivatives of ethane, which avoids the unwanted formation of large amounts of heavy halogen-containing derivatives. To this end, a vinyl halide in the gaseous state is introduced continuously, at atmospheric pressure, into a reactor containing a liquid medium formed essentially of anhydrous hydrogen fluoride, maintained at a temperature between −15 and +19° C. With the aim of accelerating the reaction or of reducing the vapour pressure of hydrogen fluoride, it is envisaged in this document to add to the hydrogen fluoride various acidic or inert substances which are miscible with the latter, in an amount by weight which is less than or equal to the amount of hydrogen fluoride. In the case where vinyl chloride is used, this known process gives rise to the joint production of 1-chloro-1-fluoroethane and 1,1-difluoroethane. However, this process appears to be of little practical value. It makes it necessary, in fact, to work with a large amount of hydrogen fluoride in the reactor, which involves acute safety problems. In addition, this process does not appear to be adapted to a variable production of 1-chloro-1-fluoroethane and 1,1-difluoroethane, which would be industrially exploitable.

SUMMARY OF THE INVENTION

The aim of the present invention is to overcome the abovementioned disadvantages of the known processes and to provide a process for the preparation of 1-chloro-1-fluoroethane and/or of 1,1-difluoroethane starting from vinyl chloride, which process is of high production efficiency and which allows the relative productions of 1-chloro-1-fluoroethane and 1,1-difluoroethane to be varied within a wide range, while limiting the unwanted formation of heavy halogen-containing side products.

DETAILED DESCRIPTION OF THE INVENTION

To this end, the invention relates to a process for the manufacture of 1-chloro-1-fluoroethane and/or 1,1-difluoroethane by reaction between hydrogen fluoride and vinyl chloride in the liquid phase, which is characterized in that the hydrogen fluoride and the vinyl chloride are introduced into an organic solvent consisting of at least one saturated halogen-containing hydrocarbon.

The saturated halogen-containing hydrocarbon is preferably selected from chloro-, fluoro- or chlorofluorohydrocarbons containing from 1 to 8 carbon atoms.

The saturated halogen-containing hydrocarbon of the solvent may be a halogen-containing hydrocarbon which is external to the reaction, that is to say a compound other than those which are formed from vinyl chloride. Halogen-containing hydrocarbons external to the reaction which are suitable in the process according to the invention are, in particular, trichloromethane, tetrachloromethane, 1,2-dichloroethane, 1,1,2-trichloroethane, 1,1,2,2-tetrachloroethane and 1,2,3-trichloropropane. Among these compounds, 1,2-dichloroethane and 1,2,3-trichloropropane are preferred. The use of such halogen-containing hydrocarbons which are external to the reaction may prove to be advantageous when the process performed discontinuously.

A saturated halogen-containing hydrocarbon of the process is advantageously used for the saturated halogen-containing hydrocarbon of the solvent. Such halogen-containing hydrocarbons are, in particular, 1-chloro-1-fluoroethane, 1,1-difluoroethane, 1,1-dichloroethane and compounds containing from 4 to 8 carbon atoms, such as 1,3-dichloro-1-fluorobutane. In a very particularly preferred manner, the solvent consists of a mixture of halogen-containing hydrocarbons which are produced in the process.

In the rest of the account, the liquid medium formed by the organic solvent, the hydrogen fluoride and vinyl chloride used, the products formed by the reaction of hydrogen fluoride and vinyl chloride and, if present, such additives as usually used in the processes for the fluorination of halogen-containing hydrocarbons, such as catalysts, is referred to as the reaction mixture.

According to the invention, in order to observe a beneficial effect on the amount of heavy side products formed, the reaction mixture must contain, at all times, at least 55% by weight of solvent. The reaction mixture preferably contains at least 70% by weight of solvent. It is particularly preferable for it to contain at least 80t by weight of solvent. The best results are obtained with a content of solvent in the reaction mixture of greater than 90% by weight. In general the content of solvent in the reaction mixture is less than 99.5%. It is preferably less than 98.5%.

In accordance with the process according to the invention, the vinyl chloride and the hydrogen fluoride are introduced into the organic solvent. The introduction of the vinyl chloride is advantageously controlled so that, at all times, the vinyl chloride content is less than 15% of the weight of the reaction mixture. This is because when the vinyl chloride content is higher, the formation of large amounts of heavy side products is observed. It is particularly advantageous to work with a vinyl chloride content of less than 10% by weight. In a very particularly advantageous manner, it never exceeds 5% by weight. The lower the vinyl chloride content is in the reaction medium, the lower the formation of heavy side products. In practice, in order to achieve a sufficient production efficiency, it is normal to work with a vinyl chloride content in the reaction mixture at least equal to 0.1% by weight, preferably at least equal to 0.5% by weight. The introduction of hydrogen fluoride is advantageously controlled so that, at all times, the hydrogen fluoride content is less than 30% of the weight of the reaction mixture. It is particularly advantageous to work with a hydrogen fluoride content of less than 15% by weight. As a general rule, the hydrogen fluoride content in the reaction mixture is at least equal to 0.3% by weight. It is preferably at least equal to 1% by weight.

In the process according to the invention, hydrogen fluoride is advantageously introduced in a hydrogen fluoride/vinyl chloride ratio at least equal to 1. Most often, this molar ratio does not exceed 20. By appropriate control of the molar ratio between the hydrogen fluoride and the vinyl chloride introduced, a wide range of control of the relative proportions of 1-chloro-1-fluoroethane and 1,1-difluoroethane produced is achieved. When the desired product is 1-chloro-1-fluoroethane, it is preferable to work with a molar ratio of from 1.1 to 4. When the desired product is 1,1-difluoroethane, it is preferable to work with a molar ratio of from 2 to 15.

The reaction mixture may contain various additives, for example a polar, inert co-solvent such as N-methylpyrrolidone or a hydrofluorination catalyst. The presence of a catalyst is optional when the desired product is 1-chloro-1-fluoroethane. It is desirable in order to obtain 1,1-difluoroethane under conditions which may be exploited industrially. Derivatives of metals chosen from metals of groups IIIa, IVa, IVb, Va, Vb and VIb of the Periodic Table of the elements, and their mixtures, may be mentioned as catalysts which may be used. Titanium, vanadium, tantalum, molybdenum, tungsten, tin and antimony derivatives are more especially selected. The tin, molybdenum and tungsten derivatives lead to the formation of large amounts of 1,1-difluoroethane and are thus preferred when it is desired to prepare this product. In this case, tin derivatives are particularly suitable. On the other hand, the vanadium, chromium and titanium derivatives are preferred when 1-chloro-1-fluoroethane is the desired product. Halides such as chlorides, fluorides and chlorofluorides, as well as oxides and oxyhalides, are preferably used as metal derivatives. Particularly preferred catalysts for preparing 1,1-difluoroethane by the process according to the present invention are tin chlorides, fluorides and chlorofluorides, $SnCl$, being very particularly preferred. Particularly preferred catalysts for preparing 1-chloro-1-fluoroethane by the process according to the present invention are the chlorides, fluorides and chlorofluorides of vanadium or chromium, VF, being very particularly preferred.

When a catalyst is used in the process according to the invention, the amount of catalyst used may vary within a wide range. The catalyst is usually used in an amount of 0.001 to 2 mol of catalyst per kg of reaction mixture and preferably from 0.01 to 1 mol per kg.

The temperature at which the reaction is performed is generally at least 40° C. and does not exceed 130° C. It is preferably at least 50° C. and does not exceed 120° C.

The pressure is chosen so as to maintain the reaction mixture in liquid form. It varies depending on the temperature of the reaction mixture. It is generally at least equal to 2 bar. Most often, it does not exceed 50 bar.

The process according to the invention may be performed discontinuously or continuously. An advantageous embodiment of the process, which allows a suitable content of organic solvent to be maintained in the reaction mixture, consists in introducing the vinyl chloride and hydrogen fluoride reactants continuously into the reactor containing the organic solvent and in withdrawing the desired product, that is to say the 1-chloro-1-fluoroethane and/or 1,1-difluoroethane, continuously from the reaction mixture. In this advantageous embodiment, the solvent may consist, partly or totally, of products formed in the process. In particular, 1-chloro-1-fluoroethane and/or 1,1-difluoroethane may be maintained in the reactor as solvent. There is occasionally a risk of transitory formation of 1,1-dichloroethane by reaction between the hydrogen chloride produced in the process and the vinyl chloride. When maintained in the reactor as solvent, it is gradually converted to 1-chloro-1-fluoroethane and/or to 1,1-difluoroethane. Sometimes, heavy side products, that is to say compounds generally containing from 4 to 8 carbon atoms and having a boiling point above that of the desired product, such as 1,3-dichloro-1-fluorobutane, may also be formed in small amounts in the process. In this advantageous embodiment of the process, the organic solvent may thus consist of a mixture comprising 1-chloro-1-fluoroethane, 1,1-difluoroethane, 1,1-dichloroethane and heavy side products. In order to avoid the accumulation of excessive amounts of side products in the reactor, for example amounts exceeding 60% by weight of the reaction mixture, it is possible, once the reaction conditions in the reactor have been established, to withdraw a small part thereof, for example by flushing regularly.

Withdrawal of the desired product from the reaction mixture may be effected in various ways. Thus, some of the reaction mixture may be drawn off continuously, in liquid form, and subjected to a separation, for example by distillation, so as to collect separately, on the one hand, the desired product and, on the other hand, the remainder of the reaction mixture, which may be recycled into the reactor. In this embodiment which is well suited to the synthesis of 1-chloro-1-fluoroethane, high pressures, between for example 10 and 50 bar, are preferably used.

According to a particularly preferred embodiment of the invention which is applied to the synthesis of 1,1-difluoroethane, a temperature and a pressure are produced in the reactor such that the 1,1-difluoroethane formed leaves the reaction mixture continuously, in gaseous form. Advantageously, all or some of the hydrogen chloride formed by the reaction is withdrawn via the same route. In this particularly preferred embodiment of the invention, the gaseous mixture which is collected contains, besides the 1,1-difluoroethane and hydrogen chloride, a little hydrogen fluoride and vinyl chloride which have not been converted, possibly a little co-produced 1-chloro-1-fluoroethane and 1,1-dichloroethane and, when the halogen-containing hydrocarbon is a compound external to the reaction, possibly a little of this halogen-containing hydrocarbon. This gaseous mixture may be subjected to one or more separation techniques which are known per se, for example by distillation, so as to collect the 1,1-difluoroethane in pure form, while the other products, except for the hydrogen chloride, may be recycled into the reactor.

According to this particularly preferred embodiment of the invention, the reaction temperature and pressure are controlled in order, on the one hand, to ensure that the reaction mixture is maintained in the liquid phase and, on the other hand, to allow the 1,1-difluoroethane to leave the reaction mixture in gaseous form, while maintaining the major part of the vinyl chloride, 1-chloro-1-fluoroethane and hydrogen fluoride in liquid form. Generally, temperatures between 60 and 120° C. for example are used. Temperatures between 80 and 110° C. have proved to be advantageous. Generally, pressures between 2 and 30 bar for example are used. Pressures of between 5 and 20 bar have proved to be advantageous.

The duration of the reaction which is necessary for ensuring an optimum yield of 1-chloro-1-fluoroethane and/or of 1,1-difluoroethane is variable, depending on the operating conditions and, in practice, may easily be determined experimentally. When the process is carried out continuously, the usual residence time of the vinyl chloride in the reactor, that is to say the ratio between the volume of reaction mixture contained in the reactor and the total flow rate of vinyl chloride and of hydrogen fluoride in the liquid state is generally from 0.1 to 5 hours.

The process according to the invention may be performed in any reactor made of a material which is resistant to the working temperature and pressure and resistant to hydrogen fluoride under the working conditions of the process. Reactors made of carbon steel, of stainless steel or of alloys such as those known under the trade names MONEL, INCONEL or HASTELLOY are advantageously used. Reactors fitted with a coating made of a metal or alloy which is resistant to hydrogen fluoride, or covered with a layer of a resin which is inert under the reaction conditions, in particular fluoro resins, may also be used.

In the process according to the invention, the hydrogen fluoride and vinyl chloride may be introduced into the reaction mixture either in the liquid state or in the vapour state. On account of the presence of the organic solvent, the vinyl chloride may be introduced into the reactor even in the liquid state without bringing about the formation of large amounts of heavy side products. The process according to the invention has the great advantage of a production efficiency which is far superior to that which is possible by the known prior process in which the vinyl chloride is introduced in gaseous form into a liquid medium essentially consisting of hydrogen fluoride, while limiting the formation of heavy side products. It allows excellent selectivities and yields of 1-chloro-1-fluoroethane and 1,1-difluoroethane to be obtained, which are much superior to those obtained in the known prior processes. In addition, depending on the reaction conditions used and the nature of the catalyst which is optionally used, it allows a wide range of variation in the quantitative ratio between the 1-chloro-1-fluoroethane and the 1,1-difluoroethane formed.

EXAMPLES

The examples which follow are given with the aim of illustrating the invention, but are in no way limiting.

Example 1

(Comparison)

After having been placed under vacuum and cooled to −20° C., a stainless steel autoclave of capacity 0.5 l, fitted with a stirrer, a temperature probe, a descending tube allowing samples in liquid phase to be taken and an inlet for introduction of the reactants, was successively loaded with 127 g of liquid vinyl chloride (VC), and then with 84 g of liquid hydrogen fluoride (HF), so as to obtain an HF/VC molar ratio equal to 2. The autoclave was subsequently immersed in an oil bath preheated to a suitable temperature, so as to bring the liquid reaction mixture, which is kept stirring, to a temperature of 60° C. The reaction mixture was maintained at this temperature under autogenous pressure for one hour. The main operating conditions and the results of analysis by gas chromatography (GC) of a sample taken from the liquid reaction mixture are collated in Table I. The column "Conv. VC" expresses the degree of conversion of VC, that is to say the amount of VC converted relative to the amount of VC used. For the various products formed (151a=1-chloro-1-fluoroethane; 152a=1,1-difluoroethane; 11DCE=1,1-dichloroethane; heavy=heavy side products), the selectivity corresponds to the amount of VC converted into this product relative to the total amount of VC converted. This example shows that, under the conditions of Patent DE 859,887, that is to say with an initial VC content in the reaction mixture equal to 100 mol % of the organic compounds, heavy side products are formed in very large amounts.

Example 2

(Comparison)

A test was performed at 30° C., in the same apparatus as that used in Example 1, starting with a liquid reaction mixture consisting exclusively of VC and HF, with an HF/VC molar ratio of 50. The results obtained after one hour at 30° C. are presented in Table I. This example shows that, in the absence of saturated halogen-containing hydrocarbon in the initial liquid reaction mixture, the use of a very large excess of hydrogen fluoride does not prevent the conversion of a large fraction of the VC to heavy side products.

Example 3

(In Accordance with the Invention)

A test was performed at 60° C., in the same apparatus as that used in the above examples, starting from a liquid reaction mixture consisting of VC, 1,1-dichloroethane and HF, with an HF/VC/11DCE molar ratio of 10/1/10. The results obtained after 2 hours at 60° C. are presented in Table I. By comparison with Examples 1 and 2, Example 3 according to the invention shows that, when the reactants are diluted in a halogen-containing hydrocarbon from the start of the process, the amount of heavy side products formed is greatly reduced. In addition, this example shows that, in the absence of catalyst, a very high selectivity of 1-chloro-1-fluoroethane is obtained.

Example 4

(Comparison)

A test was performed at 60° C., in the same apparatus as that used in the above examples, starting from a liquid reaction mixture consisting of VC and HF, with an HF/VC molar ratio of 3/1, in the presence of 0.05 mol of SnCl, per mole of VC. The results obtained after reaction for 2 hours at 60° C. are presented in Table I. This example shows that, under similar conditions to those of U.S. Pat. No. 2,495,407, that is to say with an initial VC content in the liquid reaction mixture equal to 100 mol % of the organic compounds and in the presence of SnCl, as catalyst, heavy side products are formed in very large amounts.

Example 5

(In Accordance with the Invention)

The test of Example 4 was repeated in the presence of 1,2-dichloroethane (12DCE) as halogen-containing hydrocarbon (HF/VC/12DCE molar ratio=12/1/9). At the start, the reaction leads mainly to the formation of EFA-151a (close to 80% selectivity for the first few minutes). The content of HFA-151a subsequently decreases in favour of the formation of HFA-152a. Heavy formation remains limited. After reaction for 4 hours, the conversion of VC is complete. The results obtained after reaction for 4 hours at 60° C. are presented in Table I.

Examples 6 to 12
(In Accordance with the Invention)

A series of tests was performed at 80° C., in the same apparatus as that used in the above examples, starting from a liquid reaction mixture consisting of VC, HF, 1,2-dichloroethane as halogen-containing hydrocarbon and various hydrofluorination catalysts. The detailed operating conditions and the results are collated in Table I. These examples illustrate the influence of the nature of the catalyst on the quantitative distribution of the products obtained. In the absence of the catalyst or in the presence of vanadium tetrafluoride, chromium trifluoride or vanadium trichloride, the main product formed is 1-chloro-1-fluoroethane. In the presence of tin tetrachloride, molybdenum pentachloride or tungsten hexachloride, larger amounts of 1,1-difluoroethane are formed. In all cases, the amount of heavy side products remains low. Depending on the catalyst used, the process thus allows a wide range of variation in the ratio between the 1-chloro-1-fluoroethane and 1,1-difluoroethane formed.

Examples 13 and 14
(In Accordance with the Invention)

The test of Example 5 was repeated in the presence of various amounts of tin tetrachloride. The results obtained after reaction for 4 hours at 60° C. are presented in Table I. In the test of Example 14, after 6 hours at 60° C., the temperature of the reactor was subsequently brought to 80° C. After 1 hour at this temperature, the distribution of the products was as follows: HFA-151a:10%; HFA-152a:65%; 11DCE:16%; heavy side products:9%. Comparison of these examples with Examples 5 and 11 teaches that it is also possible to vary the distribution between the resulting 1-chloro-1-fluoroethane and 1,1-difluoroethane by adjusting the amount of catalyst in the solvent and/or the temperature. The amount of 1,1-difluoroethane formed increases to the detriment of the amount of 1-chloro-1-fluoroethane formed when the amount of catalyst increases or when the temperature increases, without resulting in a large variation in the amount of heavy side products formed.

Examples 15–19
(In Accordance with the Invention)

The following tests were performed continuously, at a temperature of 90° C. and at a pressure of 15 bar, in a 200 cm$^3$ stainless steel reactor fitted with a stirrer, a jacket in which an oil for heating the reactor circulates and an overflow tube for withdrawal, maintained at the same temperature as the reactor. The vinyl chloride, hydrogen fluoride and catalyst were introduced continuously into the reactor, initially containing 1-chloro-1-fluoroethane as halogen-containing hydrocarbon, maintained in liquid form at the reaction temperature by controlling the pressure in the reactor. After 5 hours of establishment of the conditions, samples of the gaseous phase and of the liquid phase overflowing from the autoclave were taken. After returning to atmospheric pressure and neutralizing in 0.1 molar caustic washing scrubber, the effluent was analysed by gas chromatography. The operating conditions and the results obtained are given in Table II. Examples 15 to 19 show the very particular advantage of performing the process according to the invention continuously, in particular for drastically limiting the formation of heavy side products. In addition, comparison of the results of Examples 15 and 16 shows that the amount of 1,1-difluoroethane formed increases to the detriment of 1-chloro-1-fluoroethane as the residence time increases. Comparison of the results of Examples 15 and 17 shows the same effect as the catalyst concentration increases. Comparison of the results of Examples 15 and 18, on the one hand, and of Examples 16 and 19, on the other hand, shows the same effect as the HF/VC ratio increases. In no case does a modification of these parameters result in a large variation in the amount of heavy side products formed.

TABLE I

| Ex. | Composition of the reaction mixt. (HF/VC/HC*) (mol. ratio) | Catalyst (mole/mol VC) | Control temp. (° C.) | Time at stable temp (h) | Conv. VC (%) | Selectivities (% VC converted) | | | |
|---|---|---|---|---|---|---|---|---|---|
| | | | | | | 151a | 152a | 11DCE | Heavy |
| 1(C) | 2/1/0 | — | 60 | 1 | 95 | 59 | <1 | 5 | 35 |
| 2(C) | 50/1/0 | — | 30 | 1 | 97 | 50 | <1 | 4 | 46 |
| 3 | 10/1/10 | — | 60 | 2 | 89 | 91 | <1 | nm* | 8 |
| 4(C) | 3/1/0 | 0.05 SnCl$_4$ | 60 | 2 | 100 | 12 | 4 | 59 | 25 |
| 5 | 12/1/9 | 0.05 SnCl$_4$ | 60 | 4 | 100 | 40 | 15 | 41 | 4 |
| 6 | 11/1/8 | — | 80 | 2 | 99 | 84 | 2 | 2 | 12 |
| 7 | 9/1/9 | 0.05 VF$_4$ | 80 | 1 | 99 | 89 | 1 | 2 | 8 |
| 8 | 11/1/9 | 0.05 CrF$_3$ | 80 | 2 | 99 | 89 | 1 | 2 | 8 |
| 9 | 11/1/9 | 0.05 VCl$_3$ | 80 | 2 | 99 | 88 | 1 | 3 | 8 |
| 10 | 12/1/10 | 0.05 WCl$_6$ | 80 | 4 | 100 | 48 | 11 | 28 | 13 |
| 11 | 12/1/10 | 0.05 SnCl$_4$ | 80 | 4 | 100 | 23 | 33 | 33 | 11 |
| 12 | 12/1/10 | 0.05 MoCl$_5$ | 80 | 4 | 100 | 28 | 27 | 38 | 7 |
| 13 | 12/1/9 | 0.01 SnCl$_4$ | 80 | 4 | 100 | 70 | 6 | 12 | 12 |
| 14 | 11/1/9 | 0.24 SnCl$_4$ | 60 | 4 | 100 | 21 | 34 | 40 | 5 |

*HC = saturated halogen-containing hydrocarbon
*nm = not measured

TABLE II

| Ex. No. | Residence time (h) | HF/VC/SnCl$_4$ Ratio (mol/mol/mol) | Conversion VC (%) | Selectivities (% VC converted) | | | | 152a/151a Ratio |
|---|---|---|---|---|---|---|---|---|
| | | | | 151a | 152a | 11DCE | Heavy | |
| 15 | 1 | 2.8/1/0.007 | 99.3 | 29 | 52 | 18 | 0.9 | 1.79:1 |
| 16 | 0.38 | 2.5/1/0.007 | 92 | 43 | 42 | 14 | 0.4 | 0.98:1 |
| 17 | 1 | 3/1/0.003 | 99.6 | 42 | 31 | 26 | 1.2 | 0.74:1 |
| 18 | 1 | 1.6/1/0.007 | 99.4 | 47 | 30 | 21 | 1.8 | 0.64:1 |
| 19 | 0.38 | 6.2/1/0.007 | 99.7 | 24 | 65 | 10 | 0.9 | 2.71:1 |

What is claimed is:

1. A process for the manufacture of 1-chloro-1-fluoroethane, 1,1-difluoroethane or mixtures thereof, with reduced formation of heavy halogen-containing side products, by reacting hydrogen fluoride and vinyl chloride reactants in the liquid phase, comprising
   (a) introducing said reactants into a liquid reaction mixture containing an organic solvent consisting of at least one saturated organic halogenated hydrocarbon so as to provide for dilution of said reactants by the halogenated hydrocarbon at all times of the reaction.

2. The process according to claim 1, wherein the saturated halogen-containing hydrocarbon is selected from chloro-, fluoro- or chlorofluorohydrocarbons containing from 1 to 8 carbon atoms.

3. The process according to claim 2, wherein the saturated halogen-containing hydrocarbon of the process is used as solvent.

4. The process according to claim 1, wherein the reaction mixture contains, at all times, at least 55% by weight of solvent.

5. The process according to claim 1, wherein the introduction of the vinyl chloride and hydrogen fluoride is controlled so that, at all times, the vinyl chloride content is less than 15% and that of hydrogen fluoride is less than 30% of the weight of the reaction mixture.

6. The process according to claim 1, wherein the molar ratio between the hydrogen fluoride and the vinyl chloride used is at least 1 and does not exceed 20.

7. The process according to claim 1, wherein the reaction is carried out in the presence of a hydrofluorination catalyst chosen from derivatives of metals of groups IIIa, IVa, IVb, Va, Vb and VIb of the Periodic Table of the elements, and their mixtures.

8. The process according to claim 1, wherein the reaction is performed at a temperature of at least 40° and not exceeding 130° C. and at a pressure at least equal to 2 bar and not exceeding 50 bar.

9. The process according to claim 1, wherein the product is withdrawn continuously from the reaction mixture.

10. The process according to claim 9, wherein the product is 1,1-difluoroethane, which is withdrawn in gaseous form.

11. A process for the manufacture of 1-chloro-1-fluoroethane, 1,1-difluoroethane or mixtures thereof y reaction between hydrogen fluoride and vinyl chloride, comprising:
   (a) providing at least prior to the reaction an organic solvent consisting of at least one saturated organic halogenated hydrocarbon;
   (b) introducing hydrogen fluoride and vinyl chloride reactants into the organic solvent;
   (c) recovering 1-chloro-1-fluoroethane, 1,1-difluoroethane or mixtures thereof.

12. The process according to claim 11, wherein the reaction mixture contains, at all times, at least 55% by weight of solvent.

13. The process according to claim 11, wherein the introduction of vinyl chloride and hydrogen fluoride is controlled so that, at all times, vinyl chloride content is less than 15% and hydrogen fluoride content is less than 30% of the weight of the reaction mixture.

14. The process according to claim 11, wherein the molar ratio between hydrogen fluoride and vinyl chloride is at least 1 and does not exceed 20.

15. The process according to claim 11, wherein the reaction is carried out in the presence of a hydrofluorination catalyst chosen from derivatives of metals of groups IIIa, IVa, IVb, Va, Vb, and VIb of the Periodic Table of the elements, and mixtures thereof.

16. The process according to claim 11, wherein the reaction is performed at a temperature of at least 40° C. and not exceed 130° C. and at a pressure equal to 2 bar and not exceeding 50 bar.

17. The process according to claim 11, wherein a desired product is continuously recovered.

18. The process according to claim 17, wherein said product is 1,1-difluoroethane, withdrawn in gaseous form.

19. The process according to claim 1, wherein said reaction is at a temperature between 80° and 110° C.

20. The process according to claim 11, wherein said reaction is at a temperature between 80° and 110° C.

21. A process for the manufacture of 1-chloro-1-fluoroethane, 1,1-difluoroethane, or mixtures thereof, with reduced formation of heavy halogen-containing side products, comprising providing a liquid reaction mixture by providing an organic solvent and introducing the hydrogen fluoride and vinyl chloride into solvent wherein hydrogen fluoride and vinyl chloride are contacted with said reaction mixture under such conditions that the vinyl chloride content is maintained in the reaction mixture at less than 15% by weight.

22. The process according to claim 21, wherein said vinyl chloride content is at least 0.1% by weight.

23. The process according to claim 21, wherein said vinyl chloride content is at least equal to 0.5% by weight and less than 10% by weight.

24. The process according to claim 21, wherein said reaction mixture contains less than 30% by weight of hydrogen fluoride.

25. The process according to claim 21, wherein the molar ratio between hydrogen fluoride and the vinyl chloride is at least 1 and does not exceed 20.

26. The process according to claim 21, wherein the reaction is carried out in the presence of a hydrofluorination catalyst selected from the group consisting of derivatives of metals of Groups IIIa, IVa, IVb, Va, Vb, and VIb of the Periodic Table of the Elements, and their mixtures.

27. The process according to claim 21, wherein the reaction is performed at a temperature of at least 40° C. and not exceeding 130° C. and at a pressure at least equal to 2 bar and not exceeding 50 bar.

28. The process according to claim 21, wherein a desired product selected from group consisting of 1-chloro-1-1 fluoroethane, 1,1-difluoroethane, and mixtures thereof is withdrawn continuously from the reaction mixture.

29. The process according to claim 28, wherein said desired product is 1,1-difluoroethane in gaseous form.

* * * * *